United States Patent
Sako et al.

(10) Patent No.: US 12,391,967 B2
(45) Date of Patent: Aug. 19, 2025

(54) PRODUCTION METHOD FOR LONG-CHAIN FATTY ACIDS AND USE THEREOF

(71) Applicant: KANEKA CORPORATION, Osaka (JP)

(72) Inventors: Fumiya Sako, Takasago (JP); Takafumi Igari, Takasago (JP); Kaoru Nishiumi, Takasago (JP); Masaru Hirano, Takasago (JP)

(73) Assignee: KANEKA CORPORATION, Osaka (JP)

( * ) Notice: Subject to any disclaimer, the term of this patent is extended or adjusted under 35 U.S.C. 154(b) by 523 days.

(21) Appl. No.: 17/760,250

(22) PCT Filed: Feb. 18, 2021

(86) PCT No.: PCT/JP2021/006040
§ 371 (c)(1),
(2) Date: Aug. 5, 2022

(87) PCT Pub. No.: WO2021/172151
PCT Pub. Date: Sep. 2, 2021

(65) Prior Publication Data
US 2023/0060958 A1 Mar. 2, 2023

(30) Foreign Application Priority Data
Feb. 28, 2020 (JP) ................. 2020-034031

(51) Int. Cl.
*C12P 7/6409* (2022.01)
*C07C 51/44* (2006.01)
*C12P 7/625* (2022.01)

(52) U.S. Cl.
CPC ............ *C12P 7/6409* (2013.01); *C07C 51/44* (2013.01); *C12P 7/625* (2013.01)

(58) Field of Classification Search
CPC  C12N 9/20; C11C 3/00; C11B 13/005; C07C 51/44
See application file for complete search history.

(56) References Cited

U.S. PATENT DOCUMENTS

| | | |
|---|---|---|
| 2011/0195484 A1 | 8/2011 | Kale |
| 2017/0107446 A1 | 4/2017 | 'T Zand et al. |
| 2017/0107453 A1 | 4/2017 | Sato et al. |
| 2018/0163156 A1 | 6/2018 | Breivik et al. |

FOREIGN PATENT DOCUMENTS

| | | |
|---|---|---|
| CN | 1916141 A | 2/2007 |
| CN | 101245359 A | 8/2008 |
| CN | 101831356 A | 9/2010 |
| CN | 101919450 A | 12/2010 |
| CN | 102325883 A | 1/2012 |
| CN | 102864189 A | 1/2013 |
| CN | 104755623 A | 7/2015 |
| CN | 106413414 A | 2/2017 |
| CN | 110499216 A | 11/2019 |
| CN | 110511966 A | 11/2019 |
| JP | 63-105683 A | 5/1988 |
| JP | 9-227892 A | 9/1997 |
| JP | 2001-54396 A | 2/2001 |
| JP | 2013-523160 A | 6/2013 |
| JP | 2018-514644 A | 6/2018 |
| WO | WO 89/11521 A1 | 11/1989 |
| WO | WO 2013/084567 A1 | 6/2013 |
| WO | WO 2014/032633 A1 | 3/2014 |
| WO | WO 2016/002868 A1 | 1/2016 |

OTHER PUBLICATIONS

Combined Chinese Office Action and Search Report issued Nov. 22, 2023, in corresponding Chinese Patent Application No. 202180014902.9 (with English Translation), 20 pages.
International Preliminary Report on Patentability and Written Opinion issued Aug. 30, 2022 in PCT/JP2021/006040 (with unedited computer generated English Translation), 8 pages.
International Search Report issued May 25, 2021 in PCT/JP2021/006040 (with unedited computer generated English Translation), 4 pages.
Japanese Office Action issued Jan. 28. 2025 in Japanese Patent Application No. 2022-503302 (with unedited computer-generated English translation), 5 pages.

*Primary Examiner* — Tekchand Saidha
(74) *Attorney, Agent, or Firm* — Oblon, McClelland, Maier & Neustadt, L.L.P.

(57) ABSTRACT

The object of an aspect of the present invention is to provide a method for producing a long-chain fatty acid, the method making it possible to prevent a coloring component from being contained in the long-chain fatty acid and recover the long-chain fatty acid at a high yield. The above problem is solved by providing a method for producing a long-chain fatty acid, the method including the steps of: (a) with use of an enzyme, decomposing, into fatty acids, triglyceride contained in a raw vegetable oil which is derived from a vegetable-derived oil-containing waste; (b) removing, by distillation, a short-chain fatty acid contained in the raw vegetable oil which has been subjected to the step (a); and (c) recovering, by short-path distillation, a long-chain fatty acid contained in the raw vegetable oil which has been subjected to the step (b).

20 Claims, No Drawings

PRODUCTION METHOD FOR LONG-CHAIN FATTY ACIDS AND USE THEREOF

CROSS-REFERENCE TO RELATED APPLICATIONS

The present application is a 35 U.S.C. § 371 national stage patent application of International patent application PCT/JP2021/006040, filed on Feb. 18, 2021, which is based on and claims the benefits of priority to Japanese Application No. 2020-034031, filed on Feb. 28, 2020. The entire contents of these applications are incorporated herein by reference.

TECHNICAL FIELD

The present invention relates to a method for producing a long-chain fatty acid and use of the long-chain fatty acid.

BACKGROUND ART

Long-chain fatty acids are used in various applications, as food additives, carbon sources for culturing organisms, and the like. Raw materials containing long-chain fatty acids in large amounts are typified by palm oil, which is produced from oil palm. However, expansion of plantations of oil palm has a problem in that it often causes environmental destruction.

Meanwhile, in order to reduce $CO_2$ from the viewpoint of life cycle assessment (LCA), it is desired to use wastes as raw materials and recover long-chain fatty acids from the wastes.

For example, Patent Literature 1 discloses a method for producing palm-based oils and fats each of which has an iodine value of not less than 58 and each of which contains γ-tocotrienol in an amount of not more than 78 ppm.

CITATION LIST

Patent Literature

[Patent Literature 1]
International Publication No. WO 2013/084567

SUMMARY OF INVENTION

Technical Problem

However, a technique of recovering a long-chain fatty acid from a waste raw material has room for improvement.

Thus, the object of an aspect of the present invention is to provide a novel production method which makes it possible to reduce the amount of a coloring component contained in a long-chain fatty acid and recover the long-chain fatty acid at a high yield.

Solution to Problem

As a result of conducting diligent studies in order to solve the above problem, the inventors of the present invention newly found it possible to produce, at a high rate of recovery, a long-chain fatty acid which has a low chromaticity, by (i) with use of an enzyme, decomposing, into fatty acids, triglyceride contained in a raw vegetable oil, (ii) removing, by distillation, a short-chain fatty acid contained in the raw vegetable oil, and then (iii) recovering, by short-path distillation, a long-chain fatty acid contained in the raw vegetable oil. As a result, the inventors of the present invention completed the present invention.

Thus, an aspect of the present invention relates to a production method including the steps of: (a) with use of an enzyme, decomposing, into fatty acids, triglyceride contained in a raw vegetable oil which is derived from a vegetable-derived oil-containing waste; (b) removing, by distillation, a short-chain fatty acid contained in the raw vegetable oil which has been subjected to the step (a); and (c) recovering, by short-path distillation, a long-chain fatty acid contained in the raw vegetable oil which has been subjected to the step (b).

A weight of the long-chain fatty acid obtained in the step (c)/a total weight of a fatty acid and the triglyceride which are contained in the raw vegetable oil in the step (a)×100     (1).

Advantageous Effects of Invention

An aspect of the present invention makes it possible to prevent a coloring component from being contained in a long-chain fatty acid and recover the long-chain fatty acid at a high yield.

DESCRIPTION OF EMBODIMENTS

The following description will discuss embodiments of the present invention in detail. Unless otherwise specified in this specification, a numerical range expressed as "A to B" means "not less than A and not more than B." All documents listed herein are incorporated herein by reference.

[1. Outline of the Present Invention]

A method for producing a long-chain fatty acid in accordance with an embodiment of the present invention (hereinafter, referred to as "present production method") is a production method including the steps of: (a) with use of an enzyme, decomposing, into fatty acids, triglyceride contained in a raw vegetable oil which is derived from a vegetable-derived oil-containing waste; (b) removing, by distillation, a short-chain fatty acid contained in the raw vegetable oil which has been subjected to the step (a); and (c) recovering, by short-path distillation, a long-chain fatty acid contained in the raw vegetable oil which has been subjected to the step (b).

A weight of the long-chain fatty acid obtained in the step (c)/a total weight of a fatty acid and the triglyceride which are contained in the raw vegetable oil in the step (a)×100     (1).

When the inventors of the present invention conducted studies on a technique of recovering a long-chain fatty acid from a waste raw material, the inventors of the present invention focused on a vegetable-derived oil-containing waste as a raw material. The inventors of the present invention found that, although a vegetable-derived oil-containing waste contains a long-chain fatty acid in a large amount, the following problems exist because the waste contains various impurities.

Due to the presence of impurities, a rate of recovery of a long-chain fatty acid is low.

Due to the presence of impurities each having a coloring component, it is difficult to obtain a long-chain fatty acid having a low chromaticity.

Under the circumstances, the inventors of the present invention conducted diligent studies on a production method which makes it possible to reduce the amount of a coloring component contained in a long-chain fatty acid and recover the long-chain fatty acid at a high yield, and consequently succeeded in obtaining the following findings.

By a production method including the steps of: with use of an enzyme, decomposing, into fatty acids, triglyceride contained in a raw vegetable oil; removing, by distillation, a short-chain fatty acid contained in the raw vegetable oil; and recovering, by short-path distillation, a long-chain fatty acid contained in the raw vegetable oil, it is possible to produce a long-chain fatty acid which has a low chromaticity (for example, not more than 700), at a high rate of recovery (for example, a rate of recovery of the long-chain fatty acid is not less than 40%, the rate of recovery being expressed by the following Expression (1): a weight of the long-chain fatty acid obtained in the step (c)/a total weight of a fatty acid and the triglyceride which are contained in the raw vegetable oil in the step (a)×100 . . . (1)).

Since the present production method makes it possible to reduce the amount of a coloring component contained in a long-chain fatty acid and recover the long-chain fatty acid at a high yield, the present production method is extremely advantageous in production of a long-chain fatty acid. Features of the present production method will be described below in detail.

[2. Method for Producing Long-Chain Fatty Acid]

The present production method is a method for producing a long-chain fatty acid, the method including the following steps (a) to (c) as essential steps.

Step (a): a step of, with use of an enzyme, decomposing, into fatty acids, triglyceride contained in a raw vegetable oil which is derived from a vegetable-derived oil-containing waste.

Step (b): a step of removing, by distillation, a short-chain fatty acid contained in the raw vegetable oil which has been subjected to the step (a).

Step (c): a step of recovering, by short-path distillation, a long-chain fatty acid contained in the raw vegetable oil which has been subjected to the step (b).

The present production method makes it possible to prevent a coloring component from being contained in a long-chain fatty acid and recover the long-chain fatty acid at a high yield. In this specification, the "long-chain fatty acid" indicates a fatty acid having 9 or more carbon atoms. The long-chain fatty acid may be one that is originally contained in a vegetable-derived oil-containing waste or may be one that is produced by decomposition of triglyceride contained in the vegetable-derived oil-containing waste. The long-chain fatty acid is not particularly limited, provided that the long-chain fatty acid is a fatty acid having 9 or more carbon atoms. However, the long-chain fatty acid is preferably a fatty acid having 12 or more carbon atoms, more preferably a fatty acid having 15 or more carbon atoms, and particularly preferably a fatty acid having 18 or more carbon atoms. In an embodiment of the present invention, examples of the long-chain fatty acid include lauric acid, myristic acid, palmitic acid, palmitoleic acid, stearic acid, oleic acid, linolic acid, linolenic acid, arachidic acid, and erucic acid.

In an embodiment of the present invention, the long-chain fatty acid can be at least one selected from the group consisting of lauric acid, myristic acid, palmitic acid, stearic acid, oleic acid, linolic acid, and linolenic acid.

(Step (a))

In the step (a) of the present production method, triglyceride contained in a raw vegetable oil which is derived from a vegetable-derived oil-containing waste is decomposed into fatty acids with use of an enzyme.

In this specification, the "vegetable-derived oil-containing waste" indicates a part which remains after valuables of a vegetable are removed and which contains an oil. For example, in a case where edible palm oil is produced from oil palm, which is a vegetable raw material, inedible palm oil other than the edible palm oil corresponds to the vegetable-derived oil-containing waste. The vegetable-derived oil-containing waste is not particularly limited, provided that the above definition is satisfied. Examples of the vegetable-derived oil-containing waste include soybean meal, rapeseed meal, sunflower meal, coffee meal, cacao hulls, sesame oil meal, cottonseed meal, tea seed meal, palm oil mill effluent (POME), palm kernel shell (PKS), empty fruit bunch (EFB), grape pomace, olive pomace, tomato pomace, sake meal, shochu meal, starch meal, whisky waste, beer meal, and soy sauce meal.

In an embodiment of the present invention, the vegetable-derived oil-containing waste can contain at least one selected from the group consisting of water, a solid content, a short-chain fatty acid, the triglyceride, a long-chain fatty acid, vitamin E, and carotenoids.

In this specification, the "raw vegetable oil" indicates a roughly refined oil which is obtained from the vegetable-derived oil-containing waste and which contains fat-soluble components. In an embodiment of the present invention, the raw vegetable oil contains at least a fatty acid and the triglyceride. A component contained in the raw vegetable oil can be easily measured by an ordinary method, for example, by high-performance liquid chromatography, gas chromatography, a method involving use of a Lovibond automatic tintometer, or the like.

In this specification, the "triglyceride" indicates a neutral fat in which three molecules of fatty acids are ester-bonded to one molecule of glycerin. The fatty acids which constitute the triglyceride are each preferably a long-chain fatty acid which is an object to be obtained by the present production method.

In the step (a), the enzyme is used to decompose the triglyceride into the fatty acids. The enzyme used in the step (a) is not particularly limited, provided that the enzyme has action of decomposing the triglyceride into the fatty acids and glycerin. Examples of such an enzyme include lipases. There are many types of lipases which differ from each other in decomposition specificity, due to the diversity of triglyceride which is a substrate. From the viewpoint of preventing accumulation of monoglyceride and diglyceride, each of which is a hydrolysate, triacylglycerol lipase EC 3.1.1.3, phospholipase A2, galactolipase, lipoprotein lipase, or acylglycerol lipase, each of which has no specificity with respect to three ester bonds ($\alpha$, $\beta$, and $\alpha'$ positions) and each of which allows decomposition to stably progress in a wide range of pHs and in a wide range of temperatures, is preferably used.

In an embodiment of the present invention, the enzyme used in the step (a) may be an enzyme contained in a microorganism. In other words, in the step (a), a microorganism having the above enzyme can also be used.

In the step (a), time for which a treatment is carried out with use of the enzyme, the amount of the enzyme to be added, a temperature at which a reaction is carried out, and the like can be set by a person skilled in the art as appropriate.

In an embodiment of the present invention, a rate of decomposition of the triglyceride in the step (a) is, for example, 90% to 100%, preferably 95% to 100%, and more preferably 97% to 100%. In a case where the rate of decomposition of the triglyceride falls within the above range, there is an advantage that it is possible to recover a long-chain fatty acid at a high yield. Note that the rate of decomposition of the triglyceride is measured and calculated by a method described in Examples.

(Step (a'))

In an embodiment of the present invention, the present production method may include the following step (a') prior to the step (a).

Step (a'): a step of separating the vegetable-derived oil-containing waste into an oil phase, an aqueous phase, and a solid content phase, and removing the aqueous phase and the solid content phase to obtain the raw vegetable oil.

In the step (a'), a method for separating the vegetable-derived oil-containing waste is not particularly limited, and any method known in this technical field can be used to carry out such separation. For example, the vegetable-derived oil-containing waste can be separated with use of a commercially available three-phase separation decanter (manufactured by IHI Corporation), which is described in Examples.

The phases (oil phase, aqueous phase and solid content phase) into which the waste is separated in the step (a') are as follows.

Oil phase: a phase containing the fat-soluble components such as the fatty acid and the triglyceride.

Aqueous phase: a phase containing water-soluble components such as potassium, sodium, calcium, and magnesium.

Solid content phase: a phase containing solid components other than the components contained in the oil phase and the components contained in the aqueous phase.

In the step (a'), it is possible to obtain the raw vegetable oil, by removing the aqueous phase and the solid content phase after separating the waste into the oil phase, the aqueous phase, and the solid content phase. In the step (a'), a method for removing the aqueous phase and the solid content phase is not particularly limited, and any method known in this technical field can be used to remove the aqueous phase and the solid content phase.

Note that the raw vegetable oil described in the above section (step (a)) applies to the raw vegetable oil in the step (a').

(Step (b))

In the step (b) of the present production method, a short-chain fatty acid contained in the raw vegetable oil which has been subjected to the step (a) is removed by distillation.

In this specification, the "short-chain fatty acid" indicates a fatty acid having 8 or less carbon atoms. The short-chain fatty acid is not particularly limited, provided that the short-chain fatty acid is a fatty acid having 8 or less carbon atoms. However, the short-chain fatty acid is preferably a fatty acid having 6 or less carbon atoms, more preferably a fatty acid having 5 or less carbon atoms, and particularly preferably a fatty acid having 4 or less carbon atoms. In an embodiment of the present invention, examples of the short-chain fatty acid include butyric acid, propionic acid, isobutyric acid, isovaleric acid, valeric acid, caproic acid, lactic acid, succinic acid, and acetic acid.

In an embodiment of the present invention, the short-chain fatty acid can be at least one selected from the group consisting of butyric acid, propionic acid, isobutyric acid, isovaleric acid, valeric acid, caproic acid, lactic acid, and succinic acid Many long-chain fatty acids contained in vegetable-derived oil-containing wastes (for example, EFB) are decomposed at 230° C. to 280° C. Therefore, in the step (b), the distillation is preferably carried out at a temperature lower than 230° C. Such a distillation temperature in the step (b) is, for example, lower than 230° C., preferably not higher than 220° C., and more preferably not higher than 210° C. In a case where the distillation temperature in the step (b) falls within the above range, there is an advantage that it is possible to remove the short-chain fatty acid while avoiding decomposition of a long-chain fatty acid.

There are many short-chain fatty acids that are classified as odor components. Therefore, there is an advantage that, by the step (b), it is possible to remove an odor component contained in the raw vegetable oil and consequently possible to obtain an odorless long-chain fatty acid.

In an embodiment of the present invention, a rate of removal of the short-chain fatty acid in the step (b) is, for example, 90% to 100%, preferably 95% to 100%, and more preferably 98% to 100%. In a case where the rate of removal of the short-chain fatty acid falls within the above range, there is an advantage that it is possible to obtain an odorless long-chain fatty acid. Note that the rate of removal of the short-chain fatty acid is measured by a method described in Examples.

In the step (b), a method for carrying out the distillation is not particularly limited, and any method known in this technical field can be used to carry out the distillation. The distillation can be, for example, by single distillation, continuous distillation, or the like disclosed, for example, in Kagaku kogaku binran (chemical engineering handbook) published by Maruzen Publishing Co., Ltd.

(Step (c))

In the step (c) of the present production method, a long-chain fatty acid contained in the raw vegetable oil which has been subjected to the step (b) is recovered by short-path distillation.

In this specification, the "short-path distillation" is synonymous with short-path distillation commonly used in this technical field. In other words, the short-path distillation indicates distillation in which a distance between an evaporation surface and a condensation surface is caused to be equal to or shorter than a mean free path of a molecule and heating is carried out under reduced pressure so that evaporation is carried out. By this process, it is possible to separate a raw material (in the step (c), the "raw vegetable oil which has been subjected to the step (b)") into a distillate and a residue. The distillate contains the long-chain fatty acid which has a relatively low boiling point, and the residue contains a coloring component which has a relatively high boiling point (for example, β-carotene, tocotrienol, tocopherol, and the like).

In the step (c), it is possible to recover only the long-chain fatty acid while avoiding inclusion of the coloring component as much as possible, by setting the pressure inside a short-path distillation apparatus (hereinafter, also referred to as a "short-path distillator") and/or the temperature of a wall surface of the short-path distillation apparatus within respective given ranges.

In an embodiment of the present invention, the pressure inside the short-path distillation apparatus in the step (c) is, for example, 5 Pa to 250 Pa, preferably 5 Pa to 200 Pa, and more preferably 10 Pa to 100 Pa.

In an embodiment of the present invention, the temperature of the wall surface of the short-path distillation apparatus in the step (c) is, for example, 150° C. to 200° C., preferably 155° C. to 198° C., and more preferably 160° C. to 195° C.

In an embodiment of the present invention, a preferable range of the temperature of the wall surface of the short-path distillation apparatus in the step (c) can vary depending on the pressure inside the short-path distillation apparatus. For example, in a case where the pressure inside the short-path distillation apparatus is 5 Pa to 30 Pa, the temperature of the wall surface of the short-path distillation apparatus is, for example, 150° C. to 180° C., preferably 152° C. to 178° C., and more preferably 155° C. to 175° C. In a case where the pressure inside the short-path distillation apparatus is more than 30 Pa and not more than 250 Pa, the temperature of the wall surface of the short-path distillation apparatus is, for example, 170° C. to 200° C., preferably 172° C. to 198° C., and more preferably 174° C. to 195° C. In a case where the pressure inside the short-path distillation apparatus and the temperature of the wall surface of the short-path distillation apparatus fall within the above respective ranges, it is possible to recover the long-chain fatty acid at a high yield while avoiding inclusion of the coloring component.

In an embodiment of the present invention, the short-path distillation in the step (c) can be carried out under conditions that (i) the pressure inside the apparatus is 5 Pa to 30 Pa and the temperature of the wall surface of the apparatus is 150° C. to 180° C. or (ii) the pressure inside the apparatus is more than 30 Pa and not more than 250 Pa and the temperature of the wall surface of the apparatus is 170° C. to 200° C.

The short-path distillation apparatus used for the short-path distillation is not particularly limited, and examples thereof include falling film evaporators, centrifugal evaporators, rising film evaporators, and wiped film evaporators. For example, as the short-path distillation apparatus, a short-path distillator manufactured by UIC, which is described later in Examples, can be used.
(Others)

The long-chain fatty acid obtained by the present production method has a lower chromaticity. Furthermore, the present production method allows for a high rate of recovery of the long-chain fatty acid.

In an embodiment of the present invention, the chromaticity of the long-chain fatty acid is, for example, not more than 700, preferably not more than 600, more preferably not more than 500, and particularly preferably not more than 460. In a case where the chromaticity of the long-chain fatty acid falls within the above range, there is an advantage that the long-chain fatty acid coloring of which is sufficiently reduced is obtained and, in a case where such a long-chain fatty acid is used, for example, to produce a polyhydroxyalkanoate (described later), it is possible to prevent a deterioration of the quality of the polyhydroxyalkanoate. The lower the chromaticity of the long-chain fatty acid is, the better it is. The lower limit of the chromaticity of the long-chain fatty acid is not particularly limited, and is, for example, not less than 50. Note that the chromaticity of the long-chain fatty acid is measured by a method described in Examples.

The rate of recovery of the long-chain fatty acid by the present production method is expressed by the following Expression (1).

The weight of the long-chain fatty acid obtained in the step (c)/the total weight of the fatty acid and the triglyceride which are contained in the raw vegetable oil in the step (a)×100          (1).

The "raw vegetable oil in the step (a)" in Expression (1) indicates the "raw vegetable oil which has not been subjected to an enzymatic treatment in the step (a)". Therefore, the "total weight of the fatty acid and the triglyceride which are contained in the raw vegetable oil in the step (a)" in Expression (1) indicates the "total weight of the fatty acid and the triglyceride which are contained in the raw vegetable oil that has not been subjected to an enzymatic treatment in the step (a)". Thus, Expression (1) "the weight of the long-chain fatty acid obtained in the step (c)/the total weight of the fatty acid and the triglyceride which are contained in the raw vegetable oil in the step (a)×100" can be also expressed as "the weight of the recovered long-chain fatty acid/the total weight of the fatty acid and the triglyceride which are contained in the raw vegetable oil×100".

In an embodiment of the present invention, the rate of recovery of the long-chain fatty acid only needs to be not less than 40%, but is preferably not less than 55%, more preferably not less than 60%, and still more preferably not less than 65%. In a case where the rate of recovery of the long-chain fatty acid falls within the above range, there is an advantage that it is possible to efficiently obtain the long-chain fatty acid at a low cost. The higher the rate of recovery of the long-chain fatty acid is, the better it is. The upper limit of the rate of recovery of the long-chain fatty acid is not particularly limited, and is, for example, not more than 100%. Note that the rate of recovery of the long-chain fatty acid is measured by a method described in Examples.

The concentration of the long-chain fatty acid included in fatty acids which are obtained by the present production method is expressed by the following Expression (2).

The amount of the long-chain fatty acid obtained in the step (c)/the amount of the fatty acids obtained in the step (c)×100          (2)

Note that Expression (2) "the amount of the long-chain fatty acid obtained in the step (c)/the amount of the fatty acids obtained in the step (c)×100" can also be expressed as "the amount of the recovered long-chain fatty acid/the amount of the recovered fatty acids×100".

In an embodiment of the present invention, the concentration of the long-chain fatty acid included in the fatty acids is, for example, not less than 93%, preferably not less than 94%, more preferably not less than 95%, and still more preferably not less than 96%, particularly preferably not less than 99%. In a case where the concentration of the long-chain fatty acid included in the fatty acids falls within the above range, there is an advantage that it is possible to efficiently obtain the long-chain fatty acid at a low cost. The higher the concentration of the long-chain fatty acid included in the fatty acids is, the better is. The upper limit of the concentration of the long-chain fatty acid included in the fatty acids is not particularly limited, and is, for example, not more than 100%. Note that the concentration of the long-chain fatty acid included in the fatty acids is measured by a method described in Examples.

[3. Method for Producing Polyhydroxyalkanoate].

In an embodiment of the present invention, provided is a method for producing a polyhydroxyalkanoate (hereinafter, referred to as "PHA"), the method including the step of culturing, with use of a long-chain fatty acid obtained by the present production method, a microorganism which is capable of producing a PHA (hereinafter, the method will be referred to as "present PHA production method", and the step will be referred to as "step (i)", for convenience). In the present PHA production method, the long-chain fatty acid which is obtained by the present production method and coloring of which is sufficiently reduced is used. Therefore, there is an advantage that it is possible to prevent a deterioration of the quality of the polyhydroxyalkanoate.

In this specification, the term "PHA" is a generic term for polymers in each of which a monomer unit is a hydroxyalkanoic acid. A hydroxyalkanoic acid which is a constituent of the PHA is not particularly limited, and examples thereof include 3-hydroxybutanoic acid, 4-hydroxybutanoic acid, 3-hydroxypropanoic acid, 3-hydroxypentanoic acid, 3-hydroxyhexanoic acid, 3-hydroxyheptanoic acid, and 3-hydroxyoctanoic acid. The polymers can be homopolymers or copolymers each of which contains two or more types of monomer units.

More specifically, examples of the PHA include poly(3-hydroxybutyrate) (P3HB), poly(3-hydroxybutyrate-co-3-hydroxyhexanoate) (P3HB3HH), poly(3-hydroxybutyrate-co-3-hydroxyvalerate) (P3HB3HV), poly(3-hydroxybutyrate-co-4-hydroxybutyrate) (P3HB4HB), poly (3-hydroxybutyrate-co-3-hydroxyoctanoate) (P3HB3HO), poly(3-hydroxybutyrate-co-3-hydroxyoctadecanoate) (P3HB3HOD), poly(3-hydroxybutyrate-co-3-hydroxydecanoate) (P3HB3HD), and poly(3-hydroxybutyrate-co-3-hydroxyvalerate-co hydroxyhexanoate) (P3HB3HV3HH).

The microorganism which is used in the present PHA production method and which is capable of producing a PHA is not particularly limited, provided that the microorganism is capable of producing the PHA within a cell of the microorganism. For example, it is possible to use a microorganism isolated from nature, a microorganism deposited at a depositary institution (for example, IFO, ATCC, or the like) for strains, or a mutant, a transformant, or the like that can be prepared from any of those microorganisms. More specific examples of the microorganism include bacteria of the genera *Cupriavidus, Alcaligenes, Ralstonia, Pseudomonas, Bacillus, Azotobacter, Nocardia*, and *Aeromonas*.

In a case where the microorganism is one that is inherently not capable of producing a PHA or one that produces only a small amount of a PHA, a transformant obtained by introducing, into the microorganism, a gene of an enzyme that synthesizes an intended PHA and/or a variant of the gene can be also used. Such a transformant is also included in the microorganism which is used in the present PHA production method and which is capable of producing a PHA. The gene of such a PHA synthetase used to prepare the transformant is not particularly limited, but is preferably a gene of a PHA synthetase derived from *A. caviae*.

By culturing the microorganism which is capable of producing a PHA under appropriate conditions, it is possible to obtain a cell of the microorganism having the PHA accumulated within the cell. A method of culturing the cell of the microorganism is not particularly limited, and can be a method described in, for example, Japanese Patent Application Publication Tokukaihei No. 05-93049.

In an embodiment of the present invention, the present PHA production method can include, after the step (i), the step of refining the PHA (for convenience, referred to as "step (ii)"). The microorganism cultured in the step (i) contains a large amount of microbial cell-derived components, which are impurities, in addition to the PHA. As such, the present PHA production method preferably includes the refining step, which is for decomposing and/or removing the impurities other than the PHA. The refining step is not particularly limited, and any physical treatment, any chemical treatment, any biological treatment, or the like that can be arrived at by a person skilled in the art can be employed. As the refining step, a refining method described in International Publication No. WO 2010/067543 is, for example, suitably employed.

In an embodiment of the present invention, the present PHA production method can further include, after the step (ii), the step of drying the PHA (for convenience, referred to as "step (iii)"). The drying step is not particularly limited, and any method that can be arrived at by a person skilled in the art can be employed. As the drying step, spray drying with use of a spray dryer can be, for example, employed. By the step (iii), it is possible to adjust the particle diameter of the PHA, as appropriate, depending on the purpose of subsequent use thereof.

The PHA obtained by the present PHA production method can be used in various applications such as paper, films, sheets, tubes, plates, rods, containers (e.g., bottle containers and the like), bags, and parts.

The present invention is not limited to the embodiments, but can be altered by a skilled person in the art within the scope of the claims. The present invention also encompasses, in its technical scope, any embodiment derived by combining technical means disclosed in differing embodiments.

Namely, the present invention encompasses the following embodiments.

<1> A method for producing a long-chain fatty acid, including the steps of:
(a) with use of an enzyme, decomposing, into fatty acids, triglyceride contained in a raw vegetable oil which is derived from a vegetable-derived oil-containing waste;
(b) removing, by distillation, a short-chain fatty acid contained in the raw vegetable oil which has been subjected to the step (a); and
(c) recovering, by short-path distillation, a long-chain fatty acid contained in the raw vegetable oil which has been subjected to the step (b).

<2> The method as described in <1>, wherein:
a chromaticity of the long-chain fatty acid is not more than 700; and
a rate of recovery of the long-chain fatty acid is not less than 40%, the rate of recovery being expressed by the following Expression (1):

$$\text{a weight of the long-chain fatty acid obtained in the step } (c)/\text{a total weight of a fatty acid and the triglyceride which are contained in the raw vegetable oil in the step } (a) \times 100 \qquad (1).$$

<3> The method as described in <1> or <2>, wherein a concentration of the long-chain fatty acid included in fatty acids is not less than 99.0%, the concentration being expressed by the following Expression (2):

$$\text{an amount of the long-chain fatty acid obtained in the step } (c)/\text{an amount of the fatty acids obtained in the step } (c) \qquad (2).$$

<4> The method as described in any one of <1> to <3>, further including, prior to the step (a), the step of:
(a') separating the vegetable-derived oil-containing waste into an oil phase, an aqueous phase, and a solid content phase, and removing the aqueous phase and the solid content phase to obtain the raw vegetable oil.

<5> The method as described in any one of <1> to <4>, wherein, in the step (c), the short-path distillation is carried out under conditions that (i) a pressure inside an apparatus is 5 Pa to 30 Pa and a temperature of a wall surface of the apparatus is 150° C. to 180° C. or (ii) the pressure inside the apparatus is more than 30 Pa and not more than 250 Pa and the temperature of the wall surface of the apparatus is 170° C. to 200° C.

<6> The method as described in any one of <1> to <5>, wherein the waste contains at least one selected from the group consisting of water, a solid content, the short-chain fatty acid, the triglyceride, the long-chain fatty acid, vitamin E, and carotenoids.

<7> The method as described in any one of <1> to <6>, wherein, in the step (a), a rate of decomposition of the triglyceride is 90% to 100%.

<8> The method as described in any one of <1> to <7>, wherein, in the step (b), a rate of removal of the short-chain fatty acid is 90% to 100%.
<9> The method as described in any one of <1> to <8>, wherein the short-chain fatty acid is at least one selected from the group consisting of butyric acid, propionic acid, isobutyric acid, isovaleric acid, valeric acid, caproic acid, lactic acid, and succinic acid.
<10> The method as described in any one of <1> to <9>, wherein the long-chain fatty acid is at least one selected from the group consisting of lauric acid, myristic acid, palmitic acid, stearic acid, oleic acid, linolic acid, and linolenic acid.
<11> A method for producing a PHA, including the step of culturing, with use of a long-chain fatty acid obtained by the method described in any one of <1> to <10>, a microorganism which is capable of producing a PHA.

EXAMPLES

The following description will discuss embodiments of the present invention in further detail on the basis of Examples. Note, however, that the present invention is not limited to Examples.
[Measuring Method and Evaluating Method]
In Examples and Comparative Examples, measurement and evaluation were carried out by the following methods.
(Rate of Decomposition of Triglyceride)
A reaction product which had been subjected to an enzymatic treatment described in the section (Enzymatic treatment, oil-water separation, and hot water washing) below was recovered in a few milliliters and kept in a warm bath at 70° C. to 80° C. for several minutes to inactivate a lipase. Subsequently, only an oil phase was recovered from a mixture which had been obtained as a result of centrifugal separation, and was used as an oil phase sample. The oil phase sample was dissolved in a mixed solution of isopropanol and hexane, and then glycerides were quantified with use of a gas chromatograph. With use of obtained results, a rate of decomposition of triglyceride was calculated by the following expression. Note that the amount of the glycerides is obtained by adding up the amount of monoglyceride, the amount of diglyceride, and the amount of the triglyceride.

The rate of decomposition of the triglyceride [%]=100−(the concentration of the glycerides after the reaction/the concentration of the glycerides before the reaction).

(Rate of Removal of Short-Chain Fatty Acid)
A rate of removal of a short-chain fatty acid was calculated by the following expression.

The rate of removal of the short-chain fatty acid [%]=(the weight of the recovered short-chain fatty acid/the weight of the short-chain fatty acid contained in a raw vegetable oil)×100

Note that the "raw vegetable oil" in the above expression indicates the "raw vegetable oil which had been subjected to the enzymatic treatment in the step (a) of the present production method".
(Measurement of Rate of Recovery of Long-Chain Fatty Acid)
A rate of recovery of a long-chain fatty acid obtained from a vegetable-derived oil-containing waste (long-chain fatty acid recovery rate) was calculated by the following expression.

The long-chain fatty acid recovery rate [%]=the weight of the recovered long-chain fatty acid/the total weight of a fatty acid and the triglyceride which were contained in the raw vegetable oil×100

Note that the "raw vegetable oil" in the above expression indicates the "raw vegetable oil which had not been subjected to the enzymatic treatment in the step (a) of the present production method".
(Measurement of Concentration of Long-Chain Fatty Acid Included in Fatty Acids)
The concentration of the long-chain fatty acid included in recovered fatty acids was measured with use of a gas chromatograph (GC-2030, manufactured by Shimadzu Corporation). The concentration of the long-chain fatty acid was calculated by the following expression.

The concentration of the long-chain fatty acid included in the fatty acids [%]=the amount of the recovered long-chain fatty acid/the amount of the recovered fatty acids×100

(Measurement of Chromaticity)
As the chromaticity of the long-chain fatty acid, a Hazen unit described in JIS K 0071-1: 2017 was employed. The chromaticity was measured with use of a Lovibond automatic tintometer PFXi995P (manufactured by Tinto meter).
(Quantitative Analysis of Vitamin E)
A quantitative analysis of vitamin E (i.e., tocopherol and tocotrienol) obtained from the vegetable-derived oil-containing waste was carried out by a method below in an external organization (Japan Food Research Laboratories Analysis Center, General Incorporated Association).
Namely, samples of Examples and Comparative Examples were collected, and saponified by adding thereto a sodium chloride solution, pyrogallol, ethanol, and potassium hydroxide. To each of the saponified samples, a sodium chloride solution and a mixed solution of hexane, 2-propanol, and ethyl acetate were added. Then, an obtained mixed solution was subjected to shake extraction. After the extraction, the mixed solution was subjected to centrifugal separation, an upper layer was taken out, and then a solvent was distilled off. A given amount of hexane was added to each of the samples after the solvent was distilled off. Subsequently, vitamin E was quantified with use of a high-performance liquid chromatograph, and each of the samples was analyzed with use of a fluorescence spectrophotometer.

Example 1

(Method for Obtaining Waste Palm Oil)
Palm empty fruit bunches generated in the step of producing palm oil from palm fruit were processed with use of a press dehydrator, and waste palm oil containing raw empty fruit bunch oil (raw EFB oil), water, and a solid content (hereinafter, simply referred to as "waste palm oil") was obtained.
(Decanter Separation)
The waste palm oil was fed to a three-phase separation decanter (manufactured by IHI Corporation), and decanter separation was carried out under conditions of 55° C., 3500 G, and 1 m$^3$/hr to 2 m$^3$/hr. By this operation, the waste palm oil was separated into the raw EFB oil, the water, the solid content at a weight ratio of 4:94:2. From the separated waste palm oil, the water and the solid content were removed to obtain the raw EFB oil. It was confirmed with use of a high-performance liquid chromatograph, a gas chromatograph, and a Lovibond automatic tintometer that the obtained raw EFB oil included a short-chain fatty acid, triglyceride, a long-chain fatty acid, vitamin A, vitamin E, carotenoids, and the like.

(Enzymatic Treatment, Oil-Water Separation, and Hot Water Washing)

To the raw EFB oil, water of the same weight as that of the raw EFB oil was added, and an obtained mixed liquid was stirred at 40° C. for 15 minutes. Subsequently, 0.03% by weight of triacylglycerol lipase EC 3.1.1.3 solution (product name: Lipase OF, manufactured by Meito Sangyo Co., Ltd.) was added to the mixed liquid of the raw EFB oil and the water. An obtained mixed liquid was stirred at 40° C. for 2 hours, and then let stand at 40° C. for 13 hours. By this operation, the triglyceride contained in the raw EFB oil was decomposed due to an enzymatic activity of the lipase, and consequently fatty acids and glycerol were produced. Then, the mixed liquid of the raw EFB oil and the water, in which mixed liquid the triglyceride was decomposed, was set to 70° C. so that oil-water separation was accelerated and the enzymatic activity of the lipase was deactivated. After the above mixed liquid was separated into an oil phase and an aqueous phase, the aqueous phase in which the glycerol and the deactivated lipase were dissolved was removed, and only the oil phase was recovered. Further, to the recovered oil phase, water of the same weight as that of the oil phase was added. An obtained mixed liquid was stirred at 70° C. for 30 minutes so as to be washed with hot water, and then let stand for 30 minutes. After the above mixed liquid was separated into an oil phase and an aqueous phase, the aqueous phase was removed, and the oil phase was recovered. The obtained oil phase was quantified with use of a gas chromatograph, and a rate of decomposition of the triglyceride was calculated. The rate of decomposition of the triglyceride in the oil phase reached 98%, and the triglyceride had been converted into the fatty acids.

(Decompression)

The oil phase was held under conditions of 85±5° C. and 13.3 kPa for 30 minutes to 60 minutes to remove the water remaining in the oil phase.

(Degassing)

The oil phase which had been subjected to the decompression was preheated to 80° C. Subsequently, the oil phase was caused to pass through a degassing apparatus at an inner temperature of 120° C. and a pressure of 10 mbar to remove, from the oil phase, the short-chain fatty acid and the like each having a boiling point of not higher than 200° C. Note that it was confirmed, by quantitation with use of a gas chromatograph, that a rate of removal of the removed short-chain fatty acid and the like was 97%.

(Short-Path Distillation)

The oil phase which had been subjected to the degassing was fed to a short-path distillator (having a diameter of 1.2 m and a heat transfer area of 0.1 m², manufactured by UIC) at a rate of 10 kg/hr. The pressure inside the distillator was set to 50 Pa, and the rotational speed of a roll wiper was set to 100 rpm. The temperature of water used in an internal condenser was maintained at 70° C. with use of a temperature control system, and the temperature of a wall surface of the distillator was set to 175° C. By this operation, the long-chain fatty acid which had been dissolved in the oil phase evaporated from the wall surface of the distillator, and then condensed on a surface of the internal condenser. The long-chain fatty acid was then discharged outside the distillator. The discharged long-chain fatty acid was recovered, and a rate of recovery and the chromaticity of the long-chain fatty acid were measured. Table 1 shows the rate of recovery of the obtained long-chain fatty acid, the concentration of the obtained long-chain fatty acid included in obtained fatty acids, and the chromaticity of the obtained long-chain fatty acid.

Example 2

A long-chain fatty acid was obtained by the same operation as in Example 1, except that the temperature of a wall surface of a short-path distillator was set to 188° C. A rate of decomposition of triglyceride in an enzymatic treatment step reached 98%, and a rate of removal of a short-chain fatty acid and the like at a time of degassing was 97%. Table 1 shows a rate of recovery of the obtained long-chain fatty acid, the concentration of the obtained long-chain fatty acid included in obtained fatty acids, and the chromaticity of the obtained long-chain fatty acid.

Example 3

A long-chain fatty acid was obtained by the same operation as in Example 1, except that the temperature of a wall surface of a short-path distillator was set to 193° C. A rate of decomposition of triglyceride in an enzymatic treatment step reached 98%, and a rate of removal of a short-chain fatty acid and the like at a time of degassing was 97%. Table 1 shows a rate of recovery of the obtained long-chain fatty acid, the concentration of the obtained long-chain fatty acid included in obtained fatty acids, and the chromaticity of the obtained long-chain fatty acid.

Example 4

A long-chain fatty acid was obtained by the same operation as in Example 1, except that the pressure inside a short-path distillator was set to 10 Pa and the temperature of a wall surface of the short-path distillator was set to 170° C. A rate of decomposition of triglyceride in an enzymatic treatment step reached 98%, and a rate of removal of a short-chain fatty acid and the like at a time of degassing was 97%. Table 1 shows a rate of recovery of the obtained long-chain fatty acid, the concentration of the obtained long-chain fatty acid included in obtained fatty acids, and the chromaticity of the obtained long-chain fatty acid.

Example 5

A long-chain fatty acid was obtained by the same operation as in Example 4, except that the temperature of a wall surface of a short-path distillator was set to 165° C. A rate of decomposition of triglyceride in an enzymatic treatment step reached 98%, and a rate of removal of a short-chain fatty acid and the like at a time of degassing was 97%. Table 1 shows a rate of recovery of the obtained long-chain fatty acid, the concentration of the obtained long-chain fatty acid included in obtained fatty acids, and the chromaticity of the obtained long-chain fatty acid.

Example 6

A long-chain fatty acid was obtained by the same operation as in Example 4, except that the temperature of a wall surface of a short-path distillator was set to 160° C. A rate of decomposition of triglyceride in an enzymatic treatment step reached 98%, and a rate of removal of a short-chain fatty acid and the like at a time of degassing was 97%. Table 1 shows a rate of recovery of the obtained long-chain fatty acid, the concentration of the obtained long-chain fatty acid included in obtained fatty acids, and the chromaticity of the obtained long-chain fatty acid.

Comparative Example 1

A long-chain fatty acid was obtained by the same operation as in Example 1, except that an enzymatic treatment, oil-water separation, and hot water washing were not carried out. Table 1 shows a rate of recovery of the obtained long-chain fatty acid, the concentration of the obtained long-chain fatty acid included in obtained fatty acids, and the chromaticity of the obtained long-chain fatty acid.

Comparative Example 2

A long-chain fatty acid was obtained by the same operation as in Example 1, except that an enzymatic treatment in the step (a) and removal of a short-chain fatty acid in the step (b) were not carried out. A rate of decomposition of triglyceride was 0%, and a rate of removal of the short-chain fatty acid was 0%. Table 1 shows a rate of recovery of the obtained long-chain fatty acid, the concentration of the obtained long-chain fatty acid included in obtained fatty acids, and the chromaticity of the obtained long-chain fatty acid.

TABLE 1

| | Pressure inside short-path distillator [Pa] | Temperature of wall surface of short-path distillator [° C.] | Rate of recovery of long-chain fatty acid [%] | Concentration of long-chain fatty acid included in fatty acids [%] | Chromaticity |
|---|---|---|---|---|---|
| Example 1 | 50 | 175 | 66.9 | 99.4 | 274 |
| Example 2 | 50 | 188 | 88.0 | 99.5 | 393 |
| Example 3 | 50 | 193 | 91.1 | 99.6 | 440 |
| Example 4 | 10 | 170 | 88.8 | 99.5 | 444 |
| Example 5 | 10 | 165 | 84.2 | 99.5 | 455 |
| Example 6 | 10 | 160 | 77.0 | 99.5 | 194 |
| Comparative Example 1 | 50 | 175 | 32.0 | 98.8 | 244 |
| Comparative Example 2 | 50 | 175 | 8.2 | 39.0 | 170 |

[Results]

It was found, from Table 1, that, in each of Examples, it was possible to recover, at a high rate of recovery, the long-chain fatty acid having a low chromaticity, as compared with Comparative Examples. Namely, it was found that, by carrying out an enzymatic treatment step of the step (a) and a short-chain fatty acid removal step of the step (b) prior to a long-chain fatty acid recovery step of the step (c), it is possible to obtain, at a high rate of recovery, a long-chain fatty acid which is highly colorless and highly transparent (has a low chromaticity).

INDUSTRIAL APPLICABILITY

The present invention makes it possible to produce, at a high rate of recovery, a long-chain fatty acid having a low chromaticity, and therefore can be advantageously used to produce a long-chain fatty acid. Furthermore, a long-chain fatty acid obtained by the present production method can be suitably used in the fields of food, biological culture, agriculture, fishery, forestry, horticulture, medicine, and the like.

The invention claimed is:

1. A method for producing a long-chain fatty acid, the method comprising:
   (a) decomposing triglyceride contained in a raw vegetable oil into fatty acids using a lipase, wherein the raw vegetable oil is obtained from vegetable waste comprising oil;
   (b) after (a), removing a short-chain fatty acid contained in the raw vegetable oil by distillation; and
   (c) after (b), recovering a long-chain fatty acid contained in the raw vegetable oil by short-path distillation,
   wherein the long-chain fatty acid has at least 9 carbon atoms, and the short-chain fatty acid has 8 or less carbon atoms.

2. The method of claim 1, wherein
   a chromaticity of the long-chain fatty acid is 700 or less; and
   a rate of recovery of the long-chain fatty acid, which is a ratio of a weight of the long-chain fatty acid obtained in (c) to a total weight of a fatty acid and the triglyceride which are contained in the raw vegetable oil in (a)×100, is at least 40%.

3. The method of claim 1, wherein a concentration of the long-chain fatty acid, which is a ratio of an amount of the long-chain fatty acid obtained in (c) to an amount of the fatty acids obtained in (c), is at least 99.0%.

4. The method of claim 1, further comprising, prior to (a):
   (a') separating the vegetable-derived oil-containing waste into an oil phase, an aqueous phase, and a solid content phase, and removing the aqueous phase and the solid content phase to obtain the raw vegetable oil.

5. The method of claim 1, wherein the short-path distillation in (c) is carried out (i) at a pressure inside an apparatus of from 5 Pa to 30 Pa and a temperature of a wall surface of the apparatus of from 150° C. to 180° C.; or (ii) at the pressure inside the apparatus of from more than 30 Pa to 250 Pa and the temperature of the wall surface of the apparatus of from 170° C. to 200° C.

6. The method of claim 1, wherein the waste comprises at least one selected from the group consisting of water, a solid content, the short-chain fatty acid, the triglyceride, the long-chain fatty acid, vitamin E, and carotenoids.

7. The method of claim 1, wherein a rate of decomposition of the triglyceride in (a) is from 90% to 100%.

8. The method of claim 1, wherein a rate of removal of the short-chain fatty acid in (b) is from 90% to 100%.

9. The method of claim 1, wherein the short-chain fatty acid is at least one selected from the group consisting of butyric acid, propionic acid, isobutyric acid, isovaleric acid, valeric acid, caproic acid, lactic acid, and succinic acid.

10. The method of claim 1, wherein the long-chain fatty acid is at least one selected from the group consisting of lauric acid, myristic acid, palmitic acid, stearic acid, oleic acid, linolic acid, and linolenic acid.

11. A method for producing a polyhydroxyalkanoate, the method comprising:
   producing a long-chain fatty acid by the method of claim 1; and
   culturing a microorganism capable of producing a polyhydroxyalkanoate using the long-chain fatty acid.

12. The method of claim 1, wherein a rate of recovery of the long-chain fatty acid, which is a ratio of a weight of the long-chain fatty acid obtained in (c) to a total weight of a fatty acid and the triglyceride which are contained in the raw vegetable oil in (a)×100, is at least 40%.

13. The method of claim 1, wherein a rate of recovery of the long-chain fatty acid, which is a ratio of a weight of the long-chain fatty acid obtained in (c) to a total weight of a fatty acid and the triglyceride which are contained in the raw vegetable oil in (a)×100, is at least 65%.

14. The method of claim 1, wherein the distillation in (b) is carried out at a temperature of lower than 230° C.

15. The method of claim 1, wherein the distillation in (b) is carried out at a temperature of lower than 210° C.

16. The method of claim 1, wherein a rate of decomposition of the triglyceride in (a) is from 97% to 100%.

17. The method of claim 1, wherein a rate of removal of the short-chain fatty acid in (b) is from 95% to 100%.

18. The method of claim 1, wherein a chromaticity of the long-chain fatty acid is 700 or less.

19. The method of claim 1, wherein a chromaticity of the long-chain fatty acid is from 50 to 460.

20. The method of claim 1, wherein the lipase is at least one selected form the group consisting of triacylglycerol lipase EC 3.1.1.3, phospholipase A2, galactolipase, lipoprotein lipase, and acylglycerol lipase.

\* \* \* \* \*